United States Patent [19]

Rohr et al.

[11] 4,233,142
[45] Nov. 11, 1980

[54] ELECTROCHEMICAL MEASURING CELL

[75] Inventors: Franz-Josef Rohr, Abtsteinach; Hubert Holick, Lampertheim, both of Fed. Rep. of Germany

[73] Assignee: Brown, Boveri & Cie Aktiengesellschaft, Mannheim-Käfertal, Fed. Rep. of Germany

[21] Appl. No.: 935,787

[22] Filed: Aug. 22, 1978

[30] Foreign Application Priority Data

Aug. 27, 1977 [DE] Fed. Rep. of Germany ....... 2738755

[51] Int. Cl.³ ............................................. G01N 27/58
[52] U.S. Cl. .................................................. 204/195 S
[58] Field of Search ............................ 204/1 S, 195 S; 123/119 E, 119 EC; 324/29

[56] References Cited

U.S. PATENT DOCUMENTS

| | | | |
|---|---|---|---|
| Re. 28,792 | 4/1976 | Ruka et al. | 204/1 S |
| 3,841,987 | 10/1974 | Friese et al. | 204/195 S |
| 3,922,204 | 11/1975 | Tseung et al. | 204/1 T |
| 3,929,670 | 12/1975 | Kudo et al. | 252/462 X |
| 3,978,006 | 8/1976 | Topp et al. | 204/195 S X |
| 4,060,498 | 11/1977 | Kawagoshi et al. | 252/462 X |

FOREIGN PATENT DOCUMENTS 1352995  5/1974  United Kingdom ................. 204/195 S

*Primary Examiner*—G. L. Kaplan
*Attorney, Agent, or Firm*—Herbert L. Lerner

[57] ABSTRACT

An electrochemical measuring cell for determining the oxygen content in exhaust gases from internal-combustion engines and combustions having an ion-conducting solid electrolyte with a measuring electrode as a first layer on the solid electrolyte and a reference electrode as a second layer on the solid electrolyte. A third layer coats the first layer measuring electrode and contains a material with a high partial oxygen pressure to obtain a characteristic $U=f(\lambda)$ which has a small slope in the range of the air number of about 1; a material with a medium partial oxygen pressure to obtain a characteristic with a medium slope; and a material with low partial oxygen pressure to obtain a characteristic with a steep slope.

15 Claims, 5 Drawing Figures

ELECTROCHEMICAL MEASURING CELL

BACKGROUND OF THE INVENTION

1. Field of the Invention

This invention relates to an electrochemical measuring cell for determining the oxygen content in gases, especially in exhaust gases of internal-combustion engines or combustion chambers, having a solid, oxygen ion-conducting electrolyte with a first layer serving as the measuring electrode, and a second layer used as the reference electrode.

2. Description of the Prior Art

Electrochemical measuring cells of this type deliver, if their electrodes are acted upon by gases with different partial oxygen pressure, an electric voltage which is proportional to the logarithm of the ratio of the partial oxygen pressures. As the reference electrode is usually exposed to air, the partial oxygen pressure of which is known, the electric voltage delivered by the measuring cell is a direct measure for the partial oxygen pressure of the measurement gas present at the measuring electrode. If the gas to be measured contains, in addition to the oxygen, oxidizable components such as carbon monoxide, hydrogen or hydrocarbons, then the thermodynamic gas equilibrium is adjusted by the catalytic action of the measuring electrode, i.e., the oxidizable or combustible gas components are oxidized, i.e., late or post-combustion, by the oxygen present in the gas to be measured. The oxygen content of the measurement gas pretreated in this manner is determined by the measuring cell. The electric voltage delivered by the measuring cell changes in step-fashion if the gas to be measured changes from one composition which contains oxidizable components in excess, to a composition without such excess of oxidizable components or with excess oxygen; a change in the opposite direction causes the same voltage step.

This step-like change of the electric voltage occurs in the measurement of exhaust gases of internal-combustion engines or combustion chambers when the ratio of the combustion air to the fuel reaches the stoichiometric value. This ratio is characterized, as is well known, by an air number $\lambda=1$. If the air number is $\lambda<1$, this means that the combustion takes place with a deficiency of air and no excess air or oxygen is present. With an air number $\lambda>1$, excess air or oxygen is present in the fuel/air mixture.

In one known electrochemical measuring cell, German Published Non-Prosecuted Application No. 2 502 409, from which the present invention starts, there is provided on the catalytically effective layer, which serves as the measuring electrode, a further catalytically active layer which serves as a coating. This design causes a change, which is as step-like and sudden or abrupt as possible, of the electric voltage delivered by the measuring cell in the vicinity of an air number of approximately $\lambda=1$. While such a measuring cell is satisfactory for regulating or measuring a fuel/air mixture with a value of about $\lambda=1$, it is not suitable for measurement or control outside this range, as there, the electric voltage delivered by the measuring cell depends only to a very slight degree on the air number.

SUMMARY OF THE INVENTION

An object of the present invention is to provide an electrochemical measuring cell of the type mentioned at the outset, in which the delivered voltage does not change step-wise or abruptly but changes continuously or gradually as a function of the oxygen content in gases, especially in combustion exhaust gases in the range about an air number of approximately $\lambda=1$; i.e., to provide an electrochemical cell with the characteristic $U=f(\lambda)$ which has a defined and, in particular, small slope over a wide range. A further object of the invention is to provide an electrochemical measuring cell which is inexpensive and simple in structure and able to withstand thermal and mechanical stresses.

With the foregoing and other objects in view, there is provided in accordance with the invention an electrochemical measuring cell for determining the oxygen content in gases, particularly in exhaust gases from internal-combustion engines or combustion chambers, having an ion-conducting solid electrode for passage of oxygen ions through the solid electrolyte with a measuring electrode disposed as a first layer on a surface of the ion-conducting solid electrolyte and a reference electrode disposed as a second layer on a surface of the ion-conducting solid electrolyte opposite the first layer, the combination therewith of a catalytically active porous third layer coating the first layer measuring electrode, said third layer containing a material with a high partial oxygen pressure to obtain a change in voltage from the electrochemical measuring cell with change in air number with a characteristic which has a small slope in the range of the air number of about 1; a material with a medium partial oxygen pressure to obtain a characteristic with a medium slope; and a material with low partial oxygen pressure to obtain a characteristic with a steep slope.

In accordance with the invention there is provided an electrochemical measuring cell with a slight slope of the characteristic, wherein the third layer contains a material of the formula $$Me_x^I Me_y^{II} Me^{III} O_3$$

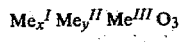

where $Me^I$ is a member selected from the group consisting of lanthanum, gadolinium and praseodymium; $Me^{II}$ is a member selected from the group consisting of strontium, calcium and barium; and $Me^{III}$ is a member selected from the group consisting of manganese, nickel, cobalt and chromium, and x has a value of 0.74 to 0.92, and y has a value of 0.08 to 0.26.

There is further provided in accordance with the invention an electrochemical measuring cell with a medium slope of the characteristic, wherein the third layer contains a mixture of an inert ceramic material such as aluminum oxide ($Al_2O_3$) or aluminum-magnesium spinel ($MgAl_2O_4$) with a material of the formula $$Me_x^I Me_y^{II} Me^{III} O_3$$

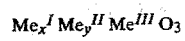

where $Me^I$ is a member selected from the group consisting of lanthanum, gadolinium and praseodymium; $Me^{II}$ is a member selected from the group consisting of strontium, calcium and barium; and $Me^{III}$ is a member selected from the group consisting of manganese, nickel, cobalt and chromium, and x has a value of 0.74 to 0.92, and y has a value of 0.08 to 0.26.

Further according to the invention, there is provided an electrochemical measuring cell with a steep slope of the characteristic, wherein the third layer contains a material of the formula $$La_x Sr_{(1-x)} Cr_x Ni_{(1-x)} O_3$$

where x has a value of 0.7 to 0.95.

Other features which are considered as characteristic for the invention are set forth in the appended claims.

Although the invention is illustrated and described herein as embodied in an electrochemical measuring cell, it is nevertheless not intended to be limited to the details shown, since various modifications may be made therein without departing from the spirit of the invention and within the scope and range of equivalents of the claims.

BRIEF DESCRIPTION OF THE DRAWINGS

The invention, however, together with additional objects and advantages thereof will be best understood from the following descripton when read in connection with the accompanying drawings, in which.

DETAILED DESCRIPTION OF THE INVENTION

Figure 1:
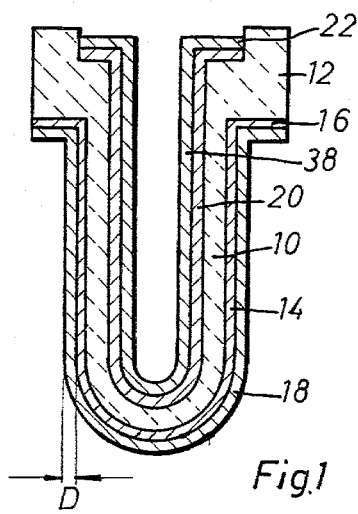
FIG. 1 diagrammatically shows an axial longitudinal cross section through a tubular measuring cell with a closed end of the electrochemical cell of the present invention.

In an electrochemical measuring cell of the invention the third layer contains a material with a high partial oxygen pressure to obtain a characteristic $U=f(\lambda)$ which has a small slope particularly in the region about an air number of approximately $\lambda=1$; a material with a medium partial oxygen pressure to obtain a characteristic with medium slope; and a material with low partial oxygen pressure to obtain a characteristic with a steep slope.

Through appropriate selection of the third layer arranged on the first layer (measuring electrode), the slope of the characteristic can therefore be set and matched to the application in question in a simple manner. Thus, one will select for measuring cells which are provided for the measurement and/or control or monitoring of the oxygen content or the air number, for instance, of internal-combustion engines, a characteristic with a slight slope, which extends largely linearly over a wide range about an air number of $\lambda=1$, e.g., from about $\lambda=0.8$ to about $\lambda=1.3$, and especially from about $\lambda=0.95$ to about $\lambda=1.05$.

A "slight" slope as used herein means a voltage change $\Delta U$ of the measuring cell of about 500 mV if the air number changes by $\Delta\lambda=0.5$. A "steep" slope means that an approximately linear voltage change of about 500 mV corresponds to a change of the air number of about $\Delta\lambda=0.05$ to 0.1.

Medium slopes are between the above-mentioned limits.

To obtain a slight slope, a third layer is required which contains a material which has a relatively high partial oxygen pressure of about $10^{-6}$ to $10^{-10}$ bar and preferably, $10^{-7}$ to $10^{-9}$ bar. For a steep slope, the layer contains a material which has a low partial oxygen pressure of about $10^{-14}$ to $10^{-18}$ bar and preferably, $10^{-15}$ to $10^{-17}$ bar. For a medium slope, the third layer contains a material, the partial oxygen pressure of which lies between the partial oxygen pressures of the above-mentioned materials, i.e., between about $10^{-10}$ and $10^{-14}$ bar and preferably, between $10^{-11}$ and $10^{-13}$ bar, at temperatures of about 800° C.

To obtain a characteristic with a slight slope, the third layer contains advantageously a material of the formula $$Me_x^I Me_y^{II} Me^{III} O_3,$$

where $Me^I$ means lanthanum, gadolinium or praseodymium; $Me^{II}$, strontium, calcium or barium; and $Me^{III}$, manganese, nickel, cobalt or chromium, and x has the values 0.74 to 0.92 and y, the values 0.08 to 0.26.

If the measuring cell is to have a characteristic with a medium slope, it has been found expedient if the third layer has a mixture of an inert ceramic material such as aluminum oxide $Al_2O_3$ or aluminum-magnesium spinel ($mgAl_2O_4$) with a material of the formula $$Me_x^I Me_y^{II} Me^{III} O_3$$

where $Me^I$ means lanthanum, gadolinium or praseodymium; $Me^{II}$, strontium, calcium or barium; and $Me^{III}$, manganese, nickel, cobalt or chromium, and x has the values 0.74 to 0.92 and y, the values 0.08 to 0.26. Particularly advantageous properties are obtained if x has the values 0.82 to 0.86 and y the values 0.14 to 0.18.

The slope of the characteristic can then be influenced within wide limits by the choice of the mixing ratio. Mixed oxides of the composition $Al_2O_3/SiO_2/MgO$ can also be used, in addition to the materials mentioned as inert materials. Thus, with a weight share of the inert material of about 10%, a slope of the characteristic is obtained which follows a characteristic with slight slope ($\Delta U = 500$ mV/$\Delta\lambda = 0.5$), and with a weight share of the inert material of about 99%, a characteristic is obtained which approaches a characteristic with steep slope ($\Delta U = 500$ mV/$\Delta\lambda = 0.1$).

A measuring cell suitable for many measuring and/or control purposes is obtained if the weight share of the inert material is between 85% and 97%.

If the measuring cell is to have a characteristic with steep slope, then the third layer advantageously contains a material of the formula $$La_x Sr_{(1-x)} Cr_x Ni_{(1-x)} O_3$$

where x has the values 0.7 to 0.95 and preferably, 0.8 to 0.85.

According to another embodiment of the invention, the third layer can contain a material of the formula Co $Cr_2O_4$, to obtain a characteristic with a steep slope.

Since the third layer according to the above-mentioned compositions contains no platinum the measuring cell according to the invention can also be used in metal-containing exhaust gases without any danger that the metals in the exhaust gases could poison the third layer, which customarily contains rare metals such as platinum. In the invention, poisoning of the third layer, which thereby falsifys the measurement results and/or shortens the life of the measuring cell, is avoided.

To make certain that the gas to be measured is subjected to the catalytic effect of the third layer for a sufficient length of time as it penetrates the third layer, it was found to be advantageous if the third layer has a thickness of at least 50 μm.

The application of the third layer becomes very simple if a third layer serving as a coating is also arranged on the respective second layer. For, then, the first and the second layer can both be provided with a third layer in one operation. Covering or protecting such layers which are not to be provided with a coating may therefore be omitted. At this point, it should be pointed out that coating the second layer serving as a reference electrode is of no significance for the functioning of the measuring cell but merely simplifies the fabrication.

Another, particularly preferred further embodiment of the invention resides in having the first and the third layer contain the same material. The first and the third layer form, so to speak, a unit. In this manner the expensive rare metal electrodes are completely avoided without having to make allowances for any disadvantages as a result thereof. As the second layer used as the reference electrode also preferably contains material according to the invention, the design of the measuring cell becomes very simple. To this should be added that it does not matter in a measuring cell designed in this manner which of the layers is used as the measuring electrode and which as the reference electrode. This is not possible in known measuring cells, because the composition of the layers serving as the electrodes is set for the function intended for it, e.g., as the reference electrode or the measuring electrode.

According to another preferred further embodiment of the invention, the third layer has a porosity which lets the gas to be measured or the reference gas pass through the third layer to a just sufficient degree. This porosity is just sufficient if the gas to be measured, on the one hand, can advance quickly through the third layer to the first layer serving as an electrode so that no appreciable delay occurs in the measurement indication in the event of a change in the concentration of the gas to be measured or the reference gas. On the other hand, attention should be paid to the fact that the porosity must be chosen so that only enough gas to be measured can flow through the third layer to the measuring electrode, in order that the gas can be catalyzed by the third and, if applicable, by the first layer as well. This aspect is of special importance for the measurement of gases with oxidizable components such as combustion exhaust gases, if these gases are to be converted to the highest possible oxidation state prior to the measurement, i.e., are to be burned up to chemical equilibrium. The comments above apply mainly for that third layer which is arranged on the first layer (measuring electrode). As the reference gas as a rule need not be processed catalytically and it composition usually does not change, the design of the porosity of that third layer which is arranged on the second layer (reference electrode), is not critical. For reasons of simplifying the fabrication, however, one will make all third layers identical.

Advantageously, the first layer has a structure which promotes the electrochemical reaction and, if required, the catalysis. A structure promoting the electrochemical reaction or the catalysis exists if it has fine-grain structure or is finely crystalline and therefore has a large active specific surface.

In choosing the thickness of the layers, it has been found to be advantageous if the first layer has a thickness of less than 30 μm and preferably less than 10 μm.

Further advantages of the invention can be seen from the following description of embodiment examples in conjunction with the diagrammatical drawings, where like parts are provided with the same reference symbols in the individual figures.

Referring to FIG. 1, the measuring cell has a tubular solid electrolyte 10 of oxygen ion-conducting material such as, for instance, zirconium oxide stabilized with calcium oxide. The lower end of the tubular electrolyte is closed in the manner of a crucible, while the upper end is open and is provided with an outward projecting collar 12. The measuring electrode is applied to the outside of the solid electrolyte 10, in the form of a first layer 14. Layer 14 contains a rare metal such as platinum, or a rare metal alloy, and is catalytically active. This means that the first layer 14 is capable of promoting, if oxygen is present, the oxidation (post-combustion) of such gas components which are not yet completely oxidized such as carbon monoxide and hydrocarbons. This property is of particular importance if the measuring cell is used for monitoring and/or measuring in exhaust gases of combustion chambers or internal-combustion engines. A design of the first layer with catalytic action is not absolutely necessary, however, if a catalytically active coating is arranged on the first layer.

The upper end 16 of the first layer 14 extends over a downward-directed shoulder which is provided at the collar 12.

Finally, a catalytically active, porous third layer 18 is provided as a coating on the first layer 14 and closes the latter off from the outside. This third layer contains materials with a defined partial oxygen pressure, preferably a material of the formula $$Me_x^I Me_y^{II} Me^{III} O_3$$

where $Me^I$ is a member selected from the group consisting of lanthanum, gadolinium and praseodymium; $Me^{II}$ is a member selected from the group consisting of strontium, calcium and barium; and $Me^{III}$ is a member selected from the group consisting of manganese, nickel, cobalt and chromium, and x has a value of 0.74 to 0.92, and y has a value of 0.08 to 0.26; a mixture of an inert ceramic material such as aluminum oxide ($Al_2O_3$) or aluminum-magnesium spinel ($MgAl_2O_4$) with a material of the formula $$Me_x^I Me_y^{II} Me^{III} O_3$$

where $Me^I$ is a member selected from the group consisting of lanthanum, gadolinium and praseodymium; $Me^{II}$ is a member selected from the group consisting of strontium, calcium and barium; and $Me^{III}$ is a member selected from the group consisting of manganese, nickel, cobalt and chromium, and x has a value of 0.74 to 0.92, and y has a value of 0.08 to 0.26; a material of the formula $$La_x Sr_{(1-x)} Cr_x Ni_{(1-x)} O_3$$

where x has a value of 0.7 to 0.95, and a material of the formula $Co Cr_2O_4$.

The inside of the tubular solid electrolyte 10 is provided with a second layer 20 which serves as the reference electrode and consists, for instance, of nickel. The upper end 22 of the second layer 20 extends over an upward-pointing shoulder, which is likewise formed at the collar 12. The electric voltage delivered by the measuring cell is taken off at the ends 16 and 22, and fed via lines to the associated measuring instrument. These ends 16 and 22 are also covered by the third layer. In order to make the layers arranged on the end 16 and, if necessary, on the end 22, impervious to gas, they can be impregnated by means of a salt solution or suspension of the layer materials named in claim 1 to 6 and subjected to a thermal treatment.

For the sake of clarity, all layers are shown very thick in the drawings, contrary to their actual thickness.

As will further be seen from FIG. 1, a third layer 38 with the composition a material with a high partial oxygen pressure to obtain a change in voltage from the electrochemical measuring cell with change in air number with a characteristic which has a slight slope in the range of the air number of about 1 wherein a slight slope means an approximately linear voltage change of the measuring cell of about 500 m V corresponds to a change of the air number of about 0.5; a material with a medium partial oxygen pressure to obtain a characteristic with a medium slope wherein a medium slope means an approximately linear voltage change of the measuring cell of about 500 m V corresponds to a change of the air number of between 0.1 and 0.5; or a material with low partial oxygen pressure to obtain a characteristic with a steep slope wherein a steep slope means an approximately linear voltage change of the measuring cell of about 500 m V corresponds to a change of the air number between 0.05 to 0.1; a material of the formula $$Me_x^I Me_y^{II} Me^{III} O_3$$

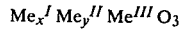

where $Me^I$ is a number selected from the group consisting of lantanum, gadolinium and praseodymium; $Me^{II}$ is a member selected from the group consisting of strontium, calcium and barium; and $Me^{III}$ is a member selected from the group consisting of manganese, nickel, cobalt and chromium, and x has a value of 0.74 to 0.92, and y has a value of 0.08 to 0.26; a mixture of an inert ceramic material such as aluminum oxide ($Al_2O_3$) or aluminum-magnesium spinel ($MgAl_2O_4$) with a material of the formula $$Me_x^I Me_y^{II} Me^{III} O_3$$

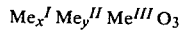

where $Me^I$ is a member selected from the group consisting of lantanum, gadolinium and praseodymium; $Me^{II}$ is a member selected from the group consisting of strontium, calcium and barium; and $Me^{III}$ is a member selected from the group consisting of manganese, nickel, cobalt and chromium, and x has a value of 0.74 to 0.92, and y has a value of 0.08 to 0.26 is likewise provided on the second layer 20. A coating on the second layer 20, which comes into contact only with the reference gas, is not necessary for influencing the slope of the characteristic, but the fabrication of the measuring cell is simplified thereby. For, if one wanted to apply a coating (third layer) only over the first layer 14, then the second layer 20 would have to be covered up and this would be cumbersome if the third layer 18 is applied by spray-sintering or immersion over the second layer 14.

During the operation, a reference gas with a defined oxygen content, such as air is fed in known manner to the interior of the measuring cell, i.e., to the second layer 20 used as the reference electrode, while the third layer 18 is exposed to the gas to be measured. Part of the gas to be measured flows through the pores of the third layer 18 to the first layer 14. By the catalytic action of the third layer 18, combustible components of the gas to be measured are burned at least to a large extent, if oxygen is present, so that the first layer 14 used as the measuring electrode is acted upon only by such gas to be measured which is largely at chemical equilibrium. The fine structure of the first layer 14, if it contains catalytically effective material, can then complete the catalysis or the post-combustion of the gas to be measured. However, this is not necessary if the porosity of the third layer 18 is chosen so that the amount of gas to be measured flowing through the pores can be completely processed catalytically by the material of the third layer 18. Otherwise, post-combustion is achieved by adjusting the porosity of the third layer 18 to the thickness D (FIG. 1) of this layer so that during operation the gas to be measured, which flows through the third layer 18 to the first layer 14, is throttled so that it can be catalytically processed (burned) in the two layers 14 and 18. Overloading and thereby, false indication of the measuring cell is therefore impossible. At the temperature required for the operation of such measuring cells such as, for instance, 200° to about 1000° C., the oxygen content of the gas to be measured is indicated by the connected measuring instrument.

Figure 4:
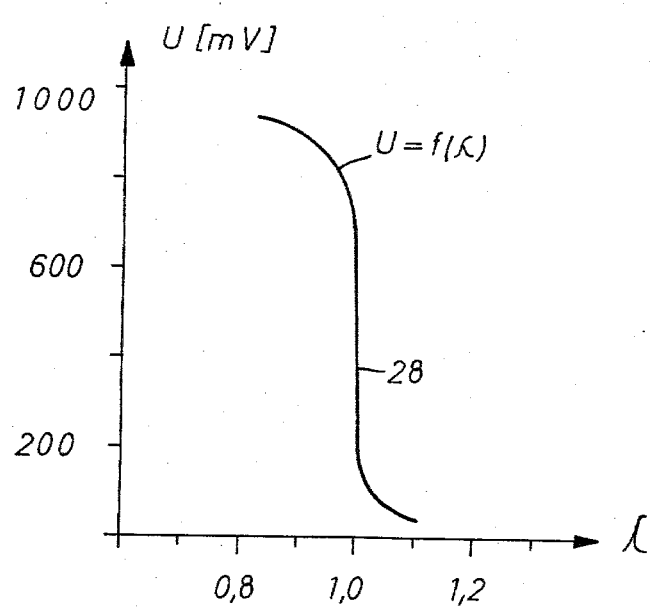

By building up the third layer with a material according to the invention, a characteristic is now obtained in such a measuring cell, which has a shape different from that of a characteristic of a measuring cell according to the state of the art. The characteristic shows the behaviour of a measuring cell in terms of change in voltage with change in air number. In FIG. 4, the characteristic of a measuring cell according to the state of the art is shown as curve 28 in a rectangular coordinate system. On the ordinate is plotted the electric voltage delivered by the measuring cell in millivolts, and on the abscissa, the air number λ of the combustion. As seen from FIG. 4, the characteristic 28 is almost parallel to the ordinate for an air number λ=1; i.e., the measurement voltage delivered by the measuring cell changes in step-fashion (see Motortechnische Zeitschrift 34 (1973), page 9). In the other regions (λ 1), the dependence of the voltage on the air number is slight.

The oxygen content remaining after the catalytic after-combustion of the gas to be measured can be plotted on the abscissa instead of the air number λ. Air numbers larger than 1 denote the presence of air, i.e., oxygen, while air numbers smaller than 1 mean a lack of air, i.e., oxygen deficiency. The numerical value of λ is a measure of the magnitude of the excess or the deficiency of oxygen.

If, on the other hand, the third layer 18 arranged on the first layer (measuring electrode) contains a material of the formula $$Me_x^I Me_y^{II} Me^{III} O_3$$

Figure 5:
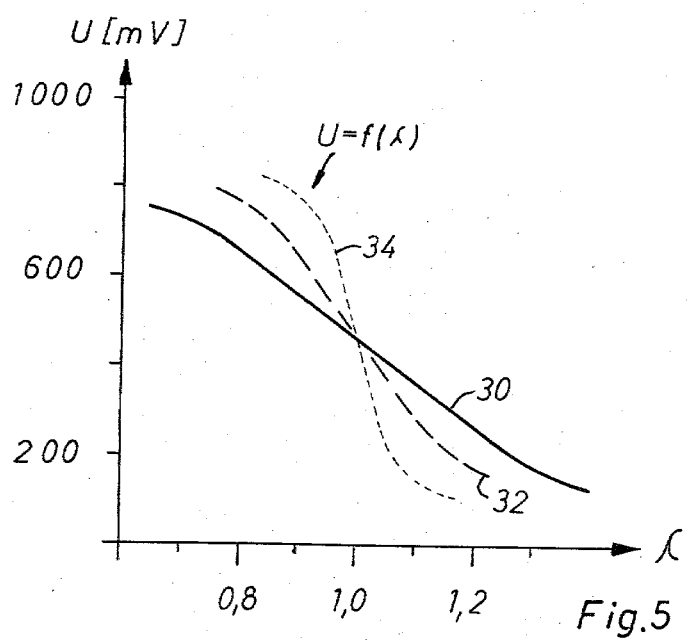

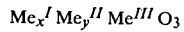

where $Me^I$ is a number selected from the group consisting of lantanum, gadolinium and praseodymium; $Me^{II}$ is a member selected from the group consisting of strontium, calcium and barium; and $Me^{III}$ is a member selected from the group consisting of manganese, nickel, cobalt and chromium, and x has a value of 0.74 to 0.92, and y has a value of 0.08 to 0.26, i.e., a material with a high partial oxygen pressure, then a characteristic ($U=f(\lambda)$) which has a slight slope is obtained. Such a characteristic 30 with a slight slope is shown in FIG. 5. As can be seen this characteristic is almost linear in the range between an air number $\lambda$ of about 0.75 to about 1.25, so that this measuring cell can be used in the above-mentioned range with high accuracy for determining the air number or of the oxygen content or oxygen deficiency and is therefore particularly well suited for measuring and control problems. If the measuring cell is to be used for measuring, then the measuring temperature and the measuring current must be kept constant and the measuring cell must be calibrated.

If the third layer arranged on the first layer (measuring electrode) contains a mixture of an inert ceramic material such as aluminum oxide ($Al_2O_3$) or aluminum-magnesium spinel ($MgAl_2O_4$) with a material of the formula $$Me_x^I Me_y^{II} Me^{III} O_3$$

where $Me^I$ is a member selected from the group consisting of lanthanum, gadolinium and praseodymium; $Me^{II}$ is a member selected from the group consisting of strontium, calcium and barium; and $Me^{III}$ is a member selected from the group consisting of manganese, nickel, cobalt and chromium, and x has a value of 0.74 to 0.92, and y has a value of 0.08 to 0.26 and has a medium partial oxygen pressure, then a characteristic 32 with medium slope is obtained, which is shown as dashed lines in FIG. 5. The range of $\lambda$ values, between which this characteristic 32 is linear, is smaller than the range belonging to the characteristic 30. As already mentioned, the mixing ratio of the material can be chosen to influence the slope of the characteristic.

If, finally, a material is used for the third layer arranged on the first layer (measuring electrode) such as a material of the formula $$La_x Sr_{(1-x)} Cr_x Ni_{(1-x)} O_3$$

where x has a value of 0.7 to 0.95; and a material of the formula $Co\, Cr_2\, O_4$ and which has a low partial oxygen pressure, then the characteristic 34 with a steep slope is obtained. This characteristic 34 is shown as dotted lines in FIG. 5.

Thus, the slope of the characteristic can be adapted to the respective application by an appropriate choice of the material for the third layer.

Figure 2:
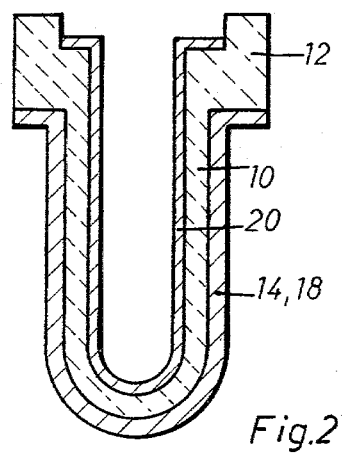
FIG. 2 is a variant of FIG. 1, in which the two outer layers form a unit.

FIG. 2 shows an embodiment variant of the measuring cell depicted in FIG. 1. The difference in substance is that the first and third layer 14, 18 as well as also the second layer 20 contain the same material. For the first and third layer 14, 18, this means that they consist of one piece i.e. both layers 14 and 18 form a unit. Such an embodiment is very simple and has no adverse effect on the desired slope of the characteristic.

Figure 3:
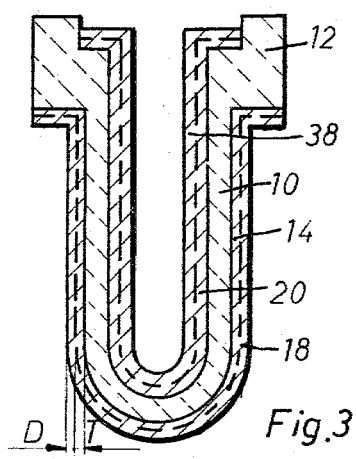
FIG. 3 is similar to FIG. 2 with a different design of the two outer layers, FIG. 4 graphically illustrates the characteristic of a measuring cell according to the state of the art, and FIG. 5 graphically illustrates the characteristics of the measuring cells according to the invention by plotting the electric voltage in millivolts delivered by the measuring cell as the ordinate against the air number as the abscissa.

FIG. 3, shows an embodiment variant of the measuring cell according to FIG. 2. The only difference from FIG. 2 is that the first and third layer 14, 18, which are combined in one unit and contain the same material, have very fine pores in the area of the first layer 14; i.e., the first layer 14 has a structure with a large specific surface. Its thickness is preferably about 10 $\mu$m. The area of the third layer 18 has a porosity which is coarser than the porosity of the first layer 14. The thickness of the third layer 18 is 50 to 100 $\mu$m.

As can be seen from FIG. 3, the second layer 20 is also provided with a third layer 38. Regarding the porosity of these two layers, what has been said in the previous paragraph also applies here. Since the reference gas need not be processed catalytically and the reference gas side of the measuring cell has no influence on the slope of the characteristic, the design of the layer unit 20, 38 is not critical, but for reasons of uniform and thereby simplified fabricaton, it is desirable to make the layers on the reference gas side exactly like the layers on the side of the gas to be measured. The layers arranged on the reference gas side of the embodiment example as shown in FIG. 3 can, of course, also be arranged as shown in FIGS. 1 and 2, i.e., there is a free choice as to the design of the reference electrode.

For preparing a material of the formula $$Me_x^I Me_y^{II} Me^{III} O_3$$

where $Me^I$ is a number selected from the group consisting of lanthanum, gadolinium and praseodymium; $Me^{II}$ is a member selected from the group consisting of strontium, calcium and barium; and $Me^{III}$ is a member selected from the group consisting of manganese, nickel, cobalt and chromium, and x has a value of 0.74 to 0.92, and y has a value of 0.08 to 0.26; a mixture of an inert ceramic material such as aluminum oxide ($Al_2O_3$) or aluminum-magnesium spinel ($MgAl_2O_4$) with a material of the formula $$Me_x^I Me_y^{II} Me^{III} O_3$$

where $Me^I$ is a member selected from the group consisting of lanthanum, gadolinium and praseodymium; $Me^{II}$ is a member selected from the group consisting of strontium, calcium and barium; and $Me^{III}$ is a member selected from the group consisting of manganese, nickel, cobalt and chromium, and x has a value of 0.74 to 0.92, and y has a value of 0.08 to 0.26; a material of the formula $$La_x Sr_{(1-x)} Cr_x Ni_{(1-x)} O_3$$

where x has a value of 0.7 to 0.95; and a material of the formula $Co\, Cr_2\, O_4$, the oxides or carbonates or nitrates of the raw materials are milled and mixed in the ratios given in these claims. Optionally, about 2 to about 5% bismuth oxide ($Bi_2O_3$), based on the weight of the mixture, are added and then mixed again. After heating for about 5 to 10 hours in air to a temperature of about 1500° C., the mixture is cooled down, and solidifies in the process of cooling. The bismuth oxide content disappears almost completely by the heating. After milling and sifting by grain size, the material is ready for use in the layers. This material is applied in known manner, for instance, by plasma spraying, spray sintering or immersing.

There is claimed:

1. In an electrochemical measuring cell for determining the oxygen content in gases, particularly in exhaust gases from internal-combustion engines or combustion chambers, having an ion-conducting solid electrolyte for passage of oxygen ions through the solid electrolyte with a measuring electrode disposed as a first layer on a surface of the ion-conducting solid electrolyte and a reference electrode disposed as a second layer on a surface of the ion-conducting solid electrolyte opposite the first layer, the combination therewith of a catalytically active porous third layer coating the first layer measuring electrode, said third layer containing a material with a medium partial oxygen pressure to obtain a change in voltage from the electrochemical measuring cell with change in air number with a characteristic which has a medium slope in the range of the air number of about 1 wherein a medium slope means an approximately linear voltage change of the measuring cell of about 500 mV corresponds to a change of the air number of between 0.1 and 0.5 and wherein the third layer contains a mixture of an inert ceramic material with a material of the formula $$Me_x^I Me_y^{II} Me^{III} O_3$$

where $Me^I$ is a member selected from the group consisting of lanthanum, gadolinium and praseodymium; $Me^{II}$ is a member selected from the group consisting of strontium, calcium and barium; and $Me^{III}$ is a member selected from the group consisting of manganese, nickel, cobalt and chromium, and x has a value of 0.74 to 0.92, and y has a value of 0.08 to 0.26.

2. Electrochemical measuring cell according to claim 1, characterized by the feature that the mixture has a content of the inert material of about 10% to 99% by weight.

3. Electrochemical measuring cell according to claim 2, wherein the content of the inert material is about 85% to 97% by weight.

4. Electrochemical measuring cell according to claim 1, wherein a third layer is arranged on the first layer and on the second layer.

5. Electrochemical measuring cell according to claim 4, wherein the first and the third layers contain the same material.

6. Electrochemical measuring cell according to claim 5, wherein all layers contain the same material.

7. In an electrochemical measuring cell for determining the oxygen content in gases, particularly in exhaust gases from internal-combustion engines or combustion chambers, having an ion-conducting solid electrolyte for passage of oxygen ions through the solid electrolyte with a measuring electrode disposed as a first layer on a surface of the ion-conducting solid electrolyte and a reference electrode disposed as a second layer on a surface of the ion-conducting solid electrolyte opposite the first layer, the combination therewith of a catalytically active porous third layer coating the first layer measuring electrode, said third layer containing a material with a low partial oxygen pressure to obtain a change in voltage from the electrochemical measuring cell with change in air number with a characteristic which has a steep slope in the range of the air number of about 1 wherein a steep slope means an approximately linear voltage change of the measuring cell of about 500 mV corresponds to a change of the air number of about 0.05 to 0.1 and wherein the third layer contains a material of the formula $$La_x Sr_{(1-x)} Cr_x Ni_{(1-x)} O_3$$

where x has a value of 0.7 to 0.95.

8. Electrochemical measuring cell according to claim 7, wherein x has a value of 0.8 to 0.85.

9. Electrochemical measuring cell according to claim 7, wherein a third layer is arranged on the first layer and on the second layer.

10. Electrochemical measuring cell according to claim 9, wherein the first and the third layers contain the same material.

11. Electrochemical measuring cell according to claim 10, wherein all layers contain the same material.

12. In an electrochemical measuring cell for determining the oxygen content in gases, particularly in exhaust gases from internal-combustion engines or combustion chambers, having an ion-conducting solid electrolyte for passage of oxygen ion through the solid electrolyte with a measuring electrode disposed as a first layer on a surface of the ion-conducting solid electrolyte and a reference electrode disposed as a second layer on a surface of the ion-conducting solid electrolyte opposite the first layer, the combination therewith of a catalytically active porous third layer coating the first layer measuring electrode, said third layer containing a material with a low partial oxygen pressure to obtain a change in voltage from the electrochemical measuring cell with change in air number with a characteristic which has a steep slope in the range of the air number of about 1 wherein a steep slope means an approximately linear voltage change of the measuring cell of about 500 mV corresponds to a change of the air number of about 0.05 to 0.1 and wherein the third layer contains a material of the formula $Co Cr_2 O_4$.

13. Electrochemical measuring cell according to claim 12, wherein a third layer is arranged on the first layer and on the second layer.

14. Electrochemical measuring cell according to claim 13, wherein the first and the third layers contain the same material.

15. Electrochemical measuring cell according to claim 14, wherein all layers contain the same material.

* * * * *